United States Patent
Barr

(10) Patent No.: US 12,156,827 B2
(45) Date of Patent: Dec. 3, 2024

(54) OVER CORRECTIVE THERAPEUTIC SCOLIOSIS BRACE

(71) Applicant: Stephen Barr, Cave Creek, AZ (US)

(72) Inventor: Stephen Barr, Cave Creek, AZ (US)

(*) Notice: Subject to any disclaimer, the term of this patent is extended or adjusted under 35 U.S.C. 154(b) by 330 days.

(21) Appl. No.: 17/932,142

(22) Filed: Sep. 14, 2022

(65) Prior Publication Data

US 2024/0082039 A1    Mar. 14, 2024

(51) Int. Cl.
*A61F 5/02* (2006.01)
*A61F 5/30* (2006.01)
*A61F 5/32* (2006.01)

(52) U.S. Cl.
CPC ............. *A61F 5/022* (2013.01); *A61F 5/024* (2013.01); *A61F 5/32* (2013.01)

(58) Field of Classification Search
CPC .......... A61F 5/022; A61F 5/024; A61F 5/026; A61F 5/028; A61F 5/32
See application file for complete search history.

(56) References Cited

U.S. PATENT DOCUMENTS

| | | | |
|---|---|---|---|
| 1,595,739 A | 8/1926 | Henry | |
| 2,687,129 A | 8/1954 | Talkish | |
| 3,029,810 A | 4/1962 | Martin | |
| 3,878,841 A | 4/1975 | Villanueva | |
| 4,175,553 A * | 11/1979 | Rosenberg | A61F 5/028 2/908 |
| 4,627,109 A * | 12/1986 | Carabelli | A61F 5/028 2/920 |
| 4,833,730 A * | 5/1989 | Nelson | A61F 5/028 2/908 |
| 5,232,424 A * | 8/1993 | Pearson | A61F 5/028 482/106 |
| 5,690,609 A * | 11/1997 | Heinze, III | A61F 5/03 2/311 |
| 10,034,791 B2 | 7/2018 | DeLuke | |
| 10,231,862 B2 | 3/2019 | Summit | |
| 2019/0388261 A1 | 12/2019 | Kang | |
| 2020/0093629 A1 | 3/2020 | Marko | |
| 2020/0179152 A1 | 6/2020 | Yampolsky | |
| 2020/0315325 A1* | 10/2020 | Truelove, III | A45F 3/04 |
| 2022/0226140 A1 | 7/2022 | Geremtzes | |

* cited by examiner

*Primary Examiner* — Camtu T Nguyen
(74) *Attorney, Agent, or Firm* — Vladimir Postnikov

(57) ABSTRACT

An adjustable over corrective therapeutic scoliosis brace configured to facilitate the correction of spinal curvature during a treatment period of a patient is provided. In some embodiments, the scoliosis brace comprises an external shell and one or more periodically adjustable modular internal pads systems. The one or more internal pad systems can be selectively moved and fixedly positioned in a plurality of positions along at least one of the lateral direction or the vertical direction within the external shell, wherein the plurality of positions are designed for periodic adjustment of the corrective force on the spinal curvature during the treatment period.

14 Claims, 6 Drawing Sheets

OVER CORRECTIVE THERAPEUTIC SCOLIOSIS BRACE

COPYRIGHT NOTICE

A portion of the disclosure of this patent document contains material that is subject to copyright protection. The copyright owner has no objection to the facsimile reproduction by anyone of the patent disclosure, as it appears in the Patent and Trademark Office patent files or records, but otherwise reserves all copyright rights whatsoever.

BACKGROUND

Field of the Invention

The present invention generally relates to external body braces and, more particularly to a scoliosis correction brace that uses a modular internal pad system that places adjustable intermittent, additional over-corrective pressure on the scoliosis curve.

Scoliosis is a medical condition associated with an abnormally curved spine, often thought to be a progressive disease, at least until adulthood. Scoliosis can have severe adverse effects on a patient's life, both physically and physiologically. One possible method of treating or managing scoliosis is surgery. Unfortunately, scoliosis surgery can be very risky. Less invasive methods of treating or managing scoliosis have traditionally included physical therapy, chiropractic therapy, or bracing, among other things.

Previous efforts have been made to provide improved comfort, support, or customizability to individual wearers. For instance, U.S. Pat. No. 170,655 describes a back and shoulder brace. This brace appears to have a single shoulder brace M, and the hip supports A and A1 appear to be disposed to the front and back of the wearer, and not under the arms. It does not appear that hip supports A, A1 can be adjusted in length.

U.S. Pat. No. 492,903 shows a flexible brace for curing spinal curvature which relies on lateral forces. The steel supports which extend up from the pelvis belt are disposed at the back and do not directly support the shoulders.

U.S. Pat. Nos. 970,781 and 1,595,739 also appear to be intended for treating spinal curvature, and do not have rigid shoulder supports under both arms of the wearer.

U.S. Pat. No. 2,687,129 describes a corrective brace for a scoliosis patient. This device includes a single rigid hip pad, a chest pad, supporting straps carried by the hip and chest pads, a tension strap, and aligned connecting bars disposed under one arm and secured to the chest and hip pads. The purpose seems to be to straighten a crooked spine by applying lateral compression.

U.S. Pat. No. 3,029,810 discloses a somewhat similar back brace that has a single adjustable strut that is disposed under one arm of the patient. It also has a pair of arm encircling connected by a shoulder strap. This brace also appears to be intended to give lateral support.

U.S. Pat. No. 3,878,841 shows an adjustable orthotic brace that has a single adjustable support extending from the side of the pelvis up to the armpit of a patient. A cushioned half crutch is connected to the upper end of the adjustable support. A harness holds the crutch in place to support one arm of the patient. A harness is provided to extend across the back of the user, and around the other shoulder to hold the half crutch in place. Each of the above devices provides rigid support only on one side of the user's body.

There are multiple solutions that have been presented in the prior art. However, these solutions are limited and restricted to their conventional architecture and installation system, and have considerable shortcomings which adversely affect the convenience with which they can be used.

The disclosed embodiments include an assembly with an advancement where a scoliosis correction brace is presented, that uses a pad system, that is used in intermittent phases to change the degree of the scoliosis curve over time. The straps are placed inside the brace at the convexity of the curve. Then the straps are pulled to put additional pressure on the scoliosis curve and help with the correction.

None of the previous inventions and patents, taken either singly or in combination, is seen to describe the embodiments disclosed herein. Hence, the disclosed embodiments propose to resolve and surmount the existing technical difficulties and eliminate the aforementioned shortcomings of the prior art.

SUMMARY OF THE INVENTION

In light of the disadvantages of the prior art, the following summary is provided to facilitate an understanding of some of the innovative features unique to the present invention and is not intended to be a full description. A full appreciation of the various aspects of the invention can be gained by taking the entire specification, claims, and abstract as a whole.

The present disclosure provides a modular and adjustable scoliosis brace that is capable of providing over-corrective forces to the spine of a patient. The scoliosis brace is additionally capable of being periodically adjusted throughout the treatment period of the patient to account for the patient's growth, as well as changes in the patient's spinal curvature. Thus, the scoliosis brace provided herein improves treatment efficacy, while reducing the overall cost of treatment. A superior level of treatment customization is achieved via the use of an external shell in conjunction with one or more adjustable modular internal pad systems. Throughout this disclosure, the term "lateral" is used to describe the anterior portions of the brace's parts when the brace is worn by a patient, referring to the portions of the parts positioned toward the front of the patient's body. Similarly, the term "dorsal" is used to describe the posterior portions of the brace's parts when the brace is worn by a patient, referring to the portions of the parts that are positioned toward the back of the patient's body.

In accordance with one embodiment of the disclosure, a modular scoliosis brace configured to aid in the correction of spinal curvature during a treatment period of a patient is provided. The scoliosis brace comprises an external shell, a closure system, a first attachment mechanism, a second attachment mechanism, and one or more modular internal pad systems, each having a lateral end and a dorsal end, the lateral ends being removably attached to the external shell with the first attachment mechanism and the dorsal ends being removably attached to the external shell with the second attachment mechanism. The external shell is configured to at least partially wrap around and conform to the patient during use. The one or more modular internal pads are selectively adjustable, such that the one or more modular internal pads can be selectively moved and fixedly positioned in a plurality of positions within the external shell with the intention of being configured to apply over-corrective pressure opposite the lateral curvature of the patient's spine, thus training the spine to return to a straighter position and reducing the scoliotic curve. The internal pad(s) are designed for rapid and easy adjustment of said over-corrective pressure by the patient as necessary during the treatment period.

In some embodiments, the external shell is comprised of a plurality of interconnected flexible lateral shells and covers much of the patient's bodice, extending from the patient's hips to their armpits.

In some embodiments, the first attachment mechanism comprises a strap and slot fastening system configured to be intermittently adjustable in order to change the over-corrective pressure applied by the one or more modular internal pads as the degree of the patient's scoliosis changes over time. In the preferred embodiment, the strap and slot system includes a plurality of vertically oriented slots located on the ends of the external shell proximate to the patient's naval region and configured to be threaded by straps connected to the lateral ends of the one or more internal pads. In some embodiments, the closure system includes straps threaded between opposite ends of the external shell to secure the external shell to the patient's bodice. In such embodiments, the straps used to adjust the one or more internal pads and the straps used to secure the external shell may utilize the same vertical slot from the plurality of vertical slots, providing for additional customization to the benefit of the patient.

In some embodiments, the second attachment mechanism comprises a button-and-buttonhole system.

This summary is provided merely for the purposes of summarizing some example embodiments, so as to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described herein will become apparent from the following detailed description and claims sections.

BRIEF DESCRIPTION OF THE DRAWINGS

The invention will be readily understood by the following detailed description in conjunction with the accompanying drawings, wherein like reference numerals designate like structural elements, and in which.

DETAILED DESCRIPTION

Figure 1:
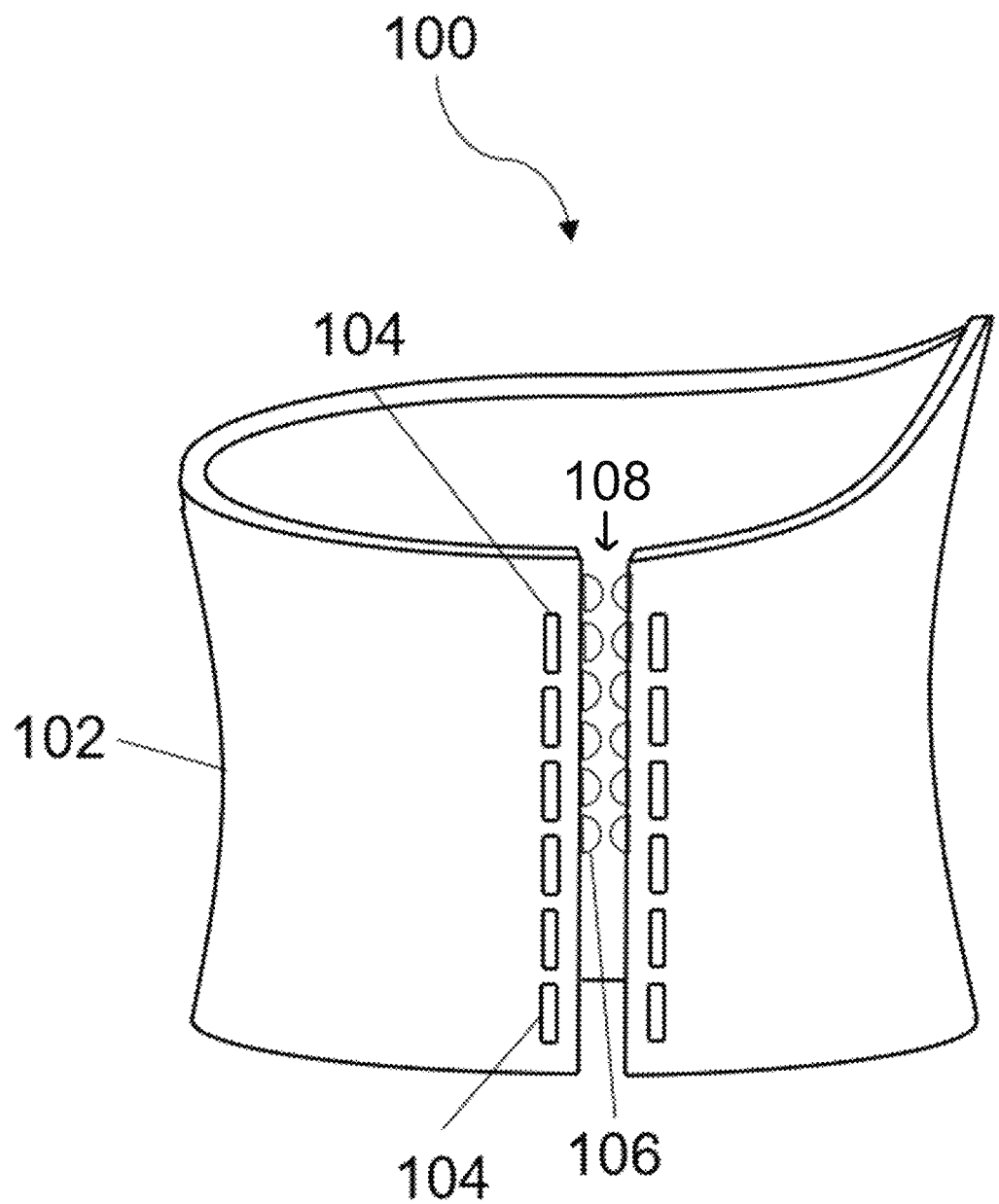
FIG. 1 is a front view of a modular scoliosis brace without any modular internal pad systems removably secured.

FIG. 1 shows a modular scoliosis brace 100 (herein referred to as "brace") without a modular internal pad system utilized. The brace 100 comprises an external shell 102, a plurality of vertically oriented slots 104 located on the ends of the external shell 102 proximate to the patient's navel region, and a plurality of buttons 106 located in a plurality of locations along the lateral direction and the vertical direction of the internal back portion of the external shell 102. The external shell 102 is configured to at least partially wrap around and conform to the patient during use. Preferably, the external shell 102 is constructed from a rigid or semi-rigid material such as plastic. The external shell 102 has an opening 108 defined by a gap between a left side and a right side of the external shell 102.

In some embodiments (not shown), the external shell 102 is comprised of a plurality of interconnected flexible lateral shells and covers much of the patient's bodice, typically extending from the patient's hips to the patient's armpits.

Figure 2:
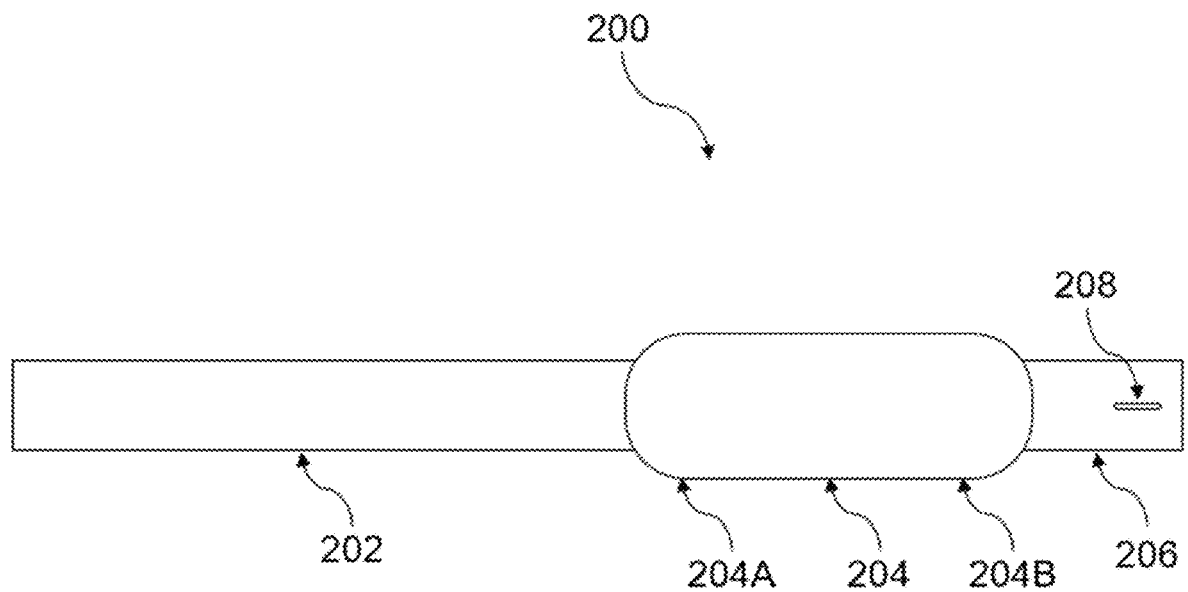
FIG. 2 is a side view of a singular modular internal pad system.

FIG. 2 is a side view of a singular modular internal pad system 200. The internal pad system 200 comprises a pad 204 having a lateral end 204A and a dorsal end 204B, a strap 202 attached to the lateral end 204A of the pad 204, a strap 206 attached to the dorsal end 204B of the pad 204 having a buttonhole 208. Preferably, the pad 204 is constructed from a rigid or semi-rigid material such as plastic and the strap portions 202, 206 are constructed from a flexible material having tensile strength such as polyester. In some embodiments, the dorsal strap 206 can include a plurality of buttonholes. In some embodiments, the strap portions are one continuous strap. In such embodiments, the one or more internal pads can be adjusted to be located at any location along the length of their straps.

Figure 3:
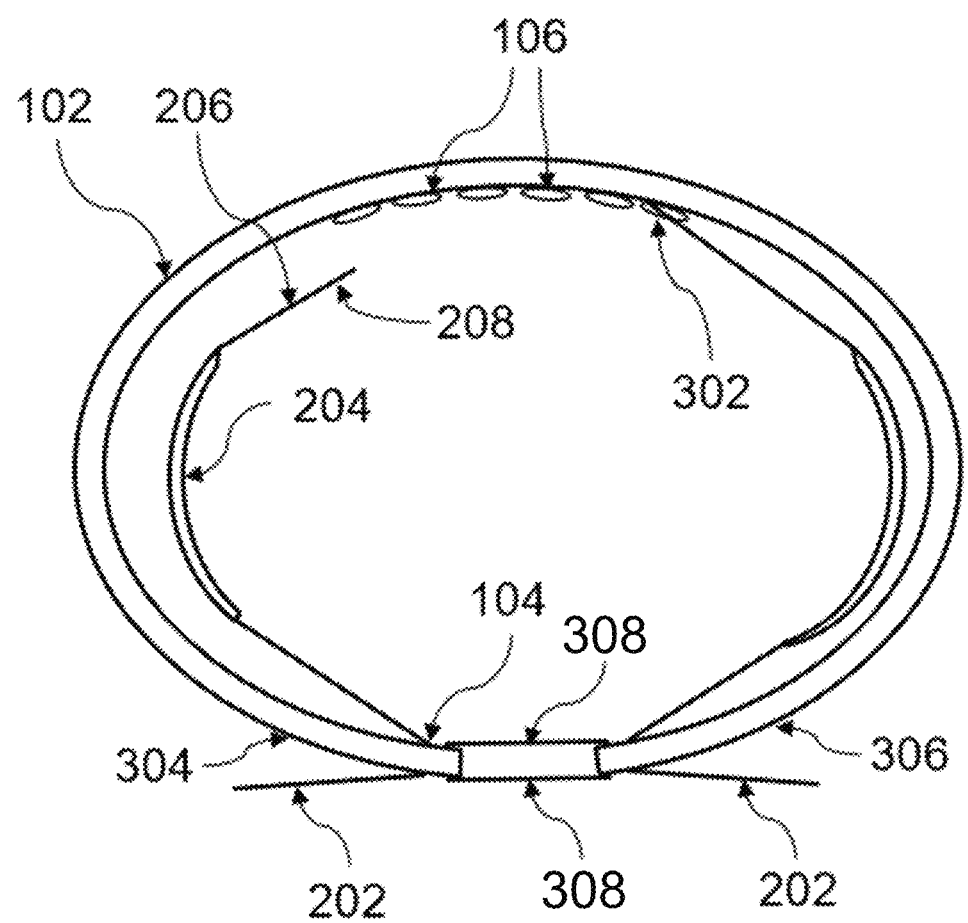
FIG. 3 is a top plan view of the modular scoliosis brace of FIG. 1 further comprising an exemplary configuration of two modular internal pad systems utilized.

FIG. 3 is a top plan view of the modular scoliosis brace of FIG. 1 further comprising an exemplary configuration of two modular internal pad systems are utilized, wherein a first attachment mechanism is a strap and slot system, a second attachment mechanism is a button and buttonhole system, and a closure system is a strap and slot system.

The first attachment mechanism that is configured to removably attach the lateral ends of the one or more internal pads to the left side 304 or right side 306 of the external shell is a strap and slot system comprising, for each pad system, a lateral strap 202 attached to the lateral end of a pad configured to be threaded through any of the vertically oriented slots 104 of the external shell 102. In some embodiments, the lateral straps utilize hook-and-loop fastener technology to removably secure said straps to either the left side 304 or right side 306 of the external shell.

The second attachment mechanism which secures the modular internal pad systems to the external shell 102 is a button and button hole fastening system comprising, for each pad system, a strap 206 attached to the dorsal end of the pad 204B, the strap having a buttonhole 208 that can be removably secured to any button of the plurality of buttons 106 by inserting the desired button through the buttonhole 302.

The closure system comprises one or more closure straps 308 threaded through two opposite slots 104. In some embodiments, the closure straps utilize hook-and-loop fastener technology to form a removably securable loop.

Figure 4:
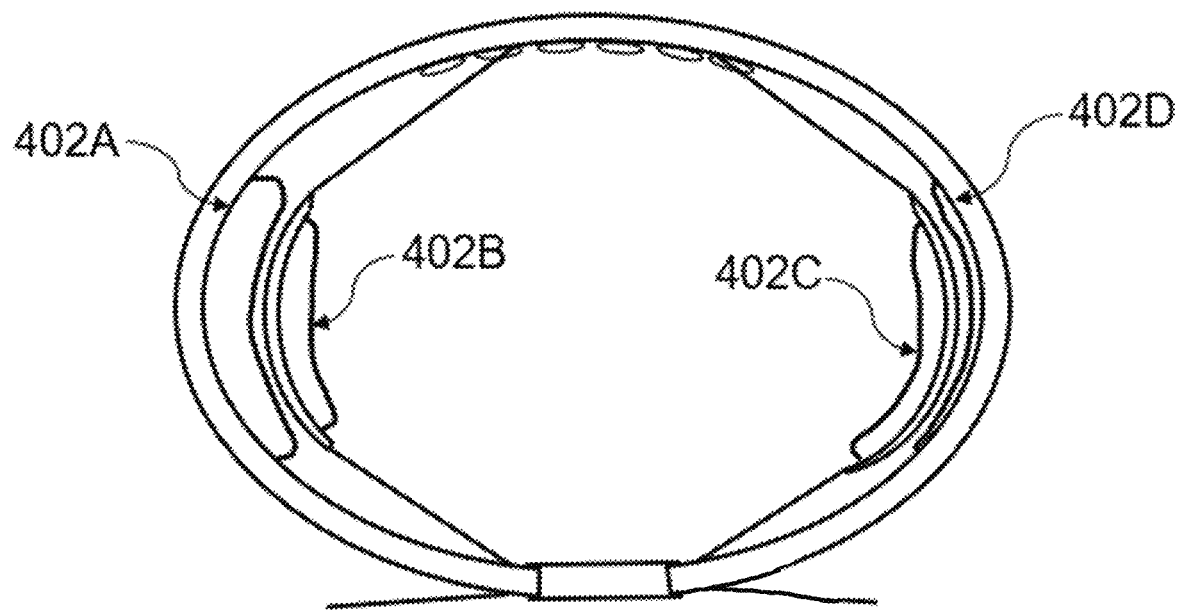
FIG. 4 is a top plan view of the modular scoliosis brace of FIG. 3 further comprising cushioning insertions.

FIG. 4 is a top plan view of the modular scoliosis brace of FIG. 3 further comprising cushioning insertions 402A—D. In this exemplary configuration, insertions 402A and 402D are attached to the inside of the external shell for the purpose of supporting the internal pads when the first attachment mechanism is not fully engaged by the patient. Insertions 402B and 402C are attached to the inside surface of the internal pads for the purpose of adding additional customization of corrective pressure to the spine of the patient and improved comfort for the wearer.

Figure 5:
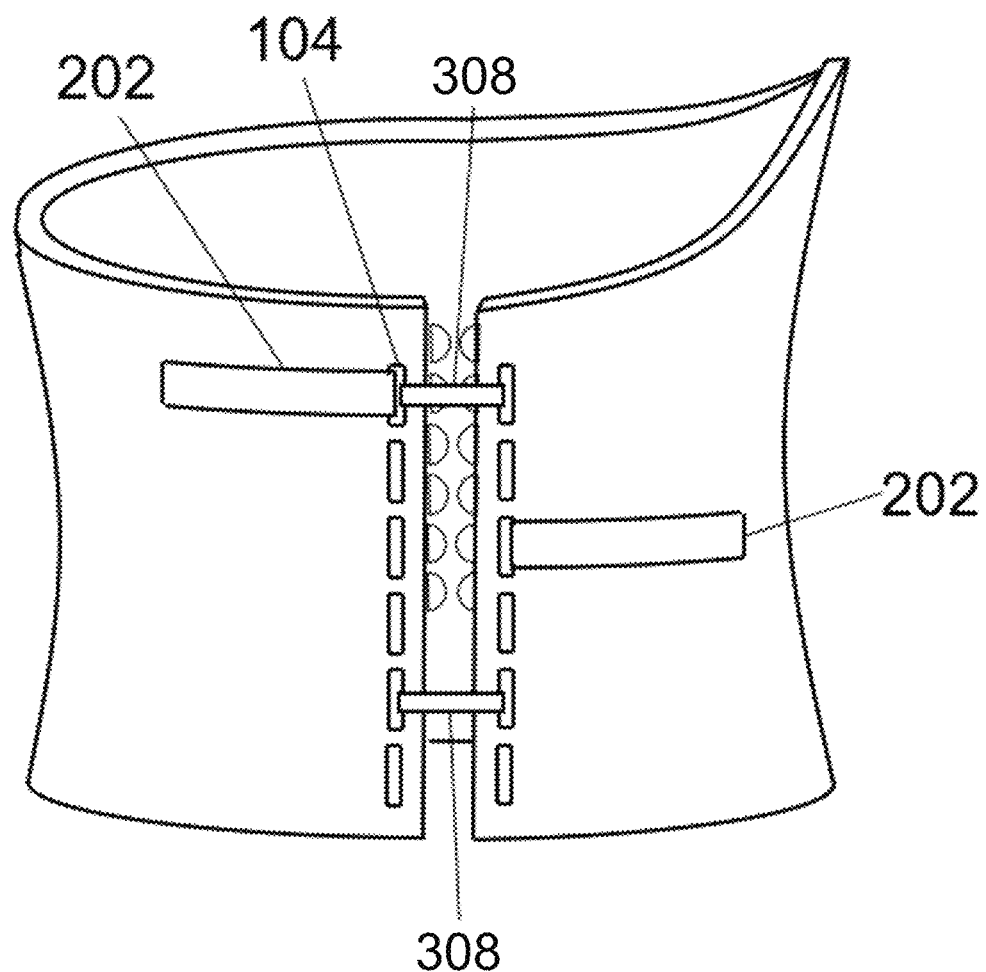
FIG. 5 is a front view of the modular scoliosis brace of FIG. 3.

FIG. 5 is a front view of the brace of FIG. 3 showing that the straps 202 used to adjust the left side internal pad system and the closure strap 306 may utilize the same slot 104, providing for additional customization to the benefit of the patient.

In some embodiments, once the strap 202 is adjusted such that the internal pad applies the desired pressure opposite the lateral curvature of the spine of a patient, the strap 202 can be removably secured to the external shell 102 by utilizing hook-and-loop fastener technology.

Figure 6:
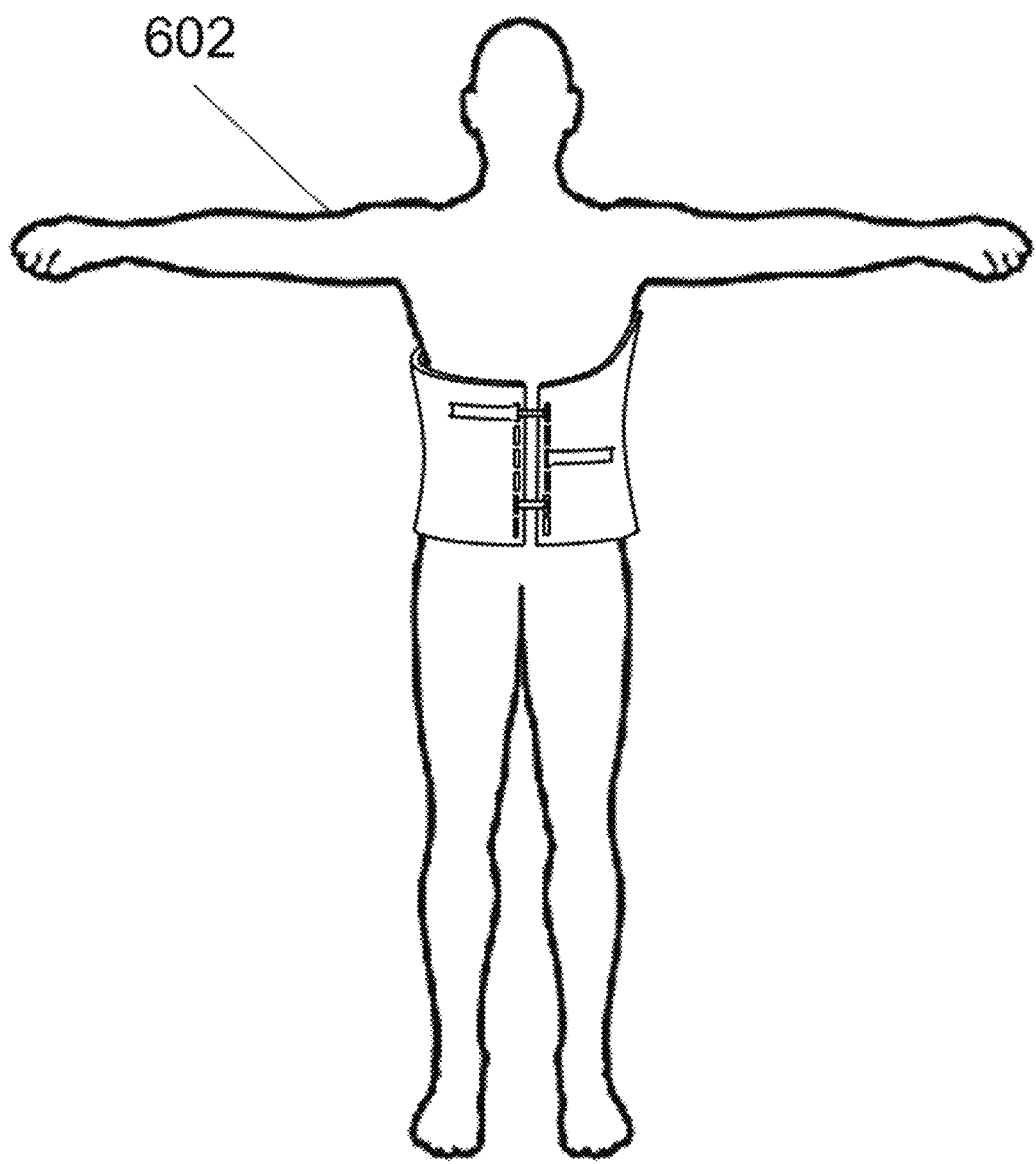
FIG. 6 illustrates a state where the modular scoliosis brace of FIG. 3 is being utilized.

FIG. 6 illustrates a state where the brace of FIG. 3 is being utilized by a patient 602. With or without the assistance of a medical professional, the patient 602 may selectively adjust the internal pad systems such that the one or more internal pads are selectively moved and fixedly positioned in a plurality of positions along at least one of the lateral direction or the vertical direction within the external shell, wherein the plurality of positions are designed for periodic adjustment of the corrective force on the spinal curvature during the treatment period. During treatment, the pad portion of the internal pad systems apply pressure opposite the lateral curvature of the spine of the patient. If additional pressure if required, the patient can readily unsecure the strap 202, pull the strap into a tighter position, and removably resecure the strap to the external shell 102 until further adjustment is required later in time.

What is claimed is:

1. A modular scoliosis brace configured to be worn by a patient comprising:
    an external shell adapted to extend laterally from a vertical direction oriented along a back of the patient and configured to at least partially wrap around and conform to the patient during use, the external shell having an opening proximate a naval region of the patient defined by a gap between a left side and a right side of the external shell;
    one or more internal pads, each having an anterior end and a posterior end, the one or more internal pads, when attached to the external shell, being configured to apply pressure opposite the lateral curvature of the spine of the patient;
    a first attachment mechanism extending from each of the one or more internal pads, the first attachment mechanism is configured to removably attach the the one or more internal pads to an anterior portion of the external shell;
    a second attachment mechanism extending from each of the one or more internal pads, the second attachment mechanism is configured to removably attach the one or more internal pads to the posterior of the external shell; and
    a closure system configured to removably attach the left side of the external shell to the right side of the external shell;
    wherein the one or more internal pads are selectively adjustable, such that the one or more internal pads being selectively moved to and fixedly positioned in one of a plurality of positions along at least one of the lateral direction or the vertical direction within the external shell,
    wherein the plurality of positions are designed for periodic adjustment of the corrective force on the spinal curvature during the treatment period.

2. The modular scoliosis brace of claim 1, wherein each of the one or more first attachment mechanisms comprise:
    a first strap;
    a plurality of vertically oriented slots proximate to a left side opening of the external shell; and
    a plurality of vertically oriented slots proximate to a right side opening of the external shell;
    wherein the first strap is configured to be threaded through a slot from the plurality of vertically oriented slots.

3. The modular scoliosis brace of claim 2, wherein the second attachment mechanism comprises:
    a second strap having one or more buttonholes; and
    a plurality of buttons located in a plurality of locations along the lateral direction and the vertical direction of the internal posterior portion of the external shell;
    wherein the one or more buttonholes are configured to be removably secured to a button from the plurality of buttons.

4. The modular scoliosis brace of claim 3, wherein the closure system comprises one or more closure straps configured to be threaded through a pair of two opposing vertically oriented slots from the plurality of vertically oriented slots, wherein the closure straps utilize hook-and-loop fasteners to form a removably securable loop.

5. The modular scoliosis brace of claim 4, wherein the one or more first straps and the one or more second straps each is a singular strap attached to the posterior of their respective pads.

6. The modular scoliosis brace of claim 5, wherein the one or more internal pads being adjustable along the length of their respective strap.

7. The modular scoliosis brace of claim 4, wherein the external shell is constructed from a rigid or semi-rigid material, the one or more first straps are constructed from a flexible material, and the one or more second straps are constructed from a flexible material.

8. The modular scoliosis brace of claim 4, further comprising:
    one or more first cushioning insertions attached to an internal surface of the external shell; and
    one or more second cushioning insertions attached to the internal surfaces of the one or more internal pads;
    wherein the one or more first cushioning insertions are configured to support the one or more internal pads when the one or more first straps are not fully engaged by the patient; and
    wherein the one or more second cushioning insertions provide additional customization of corrective pressure to the spine of the patient.

9. The modular scoliosis brace of claim 2, wherein the one or more first straps further comprise hook-and-loop fasteners to removably secure the one or more first straps to the external portion of the external shell.

10. A modular scoliosis brace configured to be worn by a patient comprising:
    an external shell adapted to extend laterally from a vertical direction oriented along a back of the patient and configured to at least partially wrap around and conform to the patient during use, the external shell having an opening proximate a naval region of the patient defined by a gap between a left side and a right side of the external shell, the left side and the right side having a plurality of vertically oriented slots proximate to the opening, the internal back portion back of the external shell having a plurality of buttons located in a plurality of locations along the lateral direction and the vertical direction;
    one or more internal pads, each having an anterior end attached to a first strap and a posterior end attached to a second strap, the first strap being configured to be threaded through a slot from the plurality of vertically oriented slots and removably attached to an external portion of the external shell using hook-and-loop fasteners, the second strap having one or more buttonholes configured to be removably attached to one or more buttons from the plurality of buttons; and one or more closure straps configured to be threaded through any pair of two opposing vertical slots from the plurality of vertically oriented slots of the external shell, the closure straps utilizing a hook-and-loop fastener to form a removably securable loop;

wherein the one or more internal pads are selectively adjustable, such that the one or more internal pads being selectively moved to and fixedly positioned in one of a plurality of positions along at least one of the lateral direction or the vertical direction within the external shell, wherein the plurality of positions are designed for periodic adjustment of the corrective force on the spinal curvature during the treatment period by adjusting the tension of the one or more first straps.

11. The modular scoliosis brace of claim 10, wherein the one or more first straps and the one or more second straps each is a singular strap attached to the posterior of their respective pads.

12. The modular scoliosis brace of claim 11, wherein the one or more internal pads being adjustable along the length of their respective strap.

13. The modular scoliosis brace of claim 10, wherein the external shell is constructed from a rigid or semi-rigid material, the one or more first straps are constructed from a flexible material, and the one or more second straps are constructed from a flexible material.

14. The modular scoliosis brace of claim 10, further comprising:

one or more first cushioning insertions attached to an internal surface of the external shell; and one or more second cushioning insertions attached to the internal surfaces of the one or more internal pads;

wherein the one or more first cushioning insertions are configured to support the one or more internal pads when the one or more first straps are not fully engaged by the patient; and wherein the one or more second cushioning insertions provide additional customization of corrective pressure to the spine of the patient.

* * * * *